United States Patent
Slobodian

[11] Patent Number: 5,884,579
[45] Date of Patent: Mar. 23, 1999

[54] WORM HARVESTER

[76] Inventor: Harry Slobodian, 5549 Pinecrest Dr., New Port Richey, Fla. 34653

[21] Appl. No.: 792,451

[22] Filed: Jan. 31, 1997

[51] Int. Cl.⁶ .......................... B68B 11/00; A01K 29/00; A63B 15/00
[52] U.S. Cl. .................. 119/6.7; 231/7; 463/47.3
[58] Field of Search .................. 47/1.3; 43/1, 98, 43/112; 119/6.7, 712, 908; 231/7; 463/47.2, 47.3; D22/117

[56] References Cited

U.S. PATENT DOCUMENTS

| | | | |
|---|---|---|---|
| D. 289,313 | 4/1987 | Shy | D22/117 |
| 1,158,473 | 11/1915 | Floyd | 231/7 |
| 1,932,237 | 10/1933 | Warner | 47/1.3 |
| 2,204,041 | 6/1940 | Jefferson | 231/7 |
| 2,253,315 | 8/1941 | Andrus | 231/7 |
| 2,450,597 | 1/1948 | Karnowski | 47/1.3 |
| 2,607,164 | 8/1952 | Fenton | 47/1.3 |
| 2,770,075 | 11/1956 | Moore | 439/874 |
| 3,362,711 | 1/1968 | Larsen et al. | 463/47.3 |
| 3,793,770 | 2/1974 | Johnson | 47/1.3 |
| 3,820,279 | 6/1974 | Sieper | 47/1.3 |
| 3,973,354 | 8/1976 | Schommer | 47/1.3 |
| 3,998,459 | 12/1976 | Henderson et al. | 463/47.3 |
| 4,817,331 | 4/1989 | Podsiadly et al. | 47/1.3 |

*Primary Examiner*—Michael J. Carone
*Assistant Examiner*—Son T. Nguyen
*Attorney, Agent, or Firm*—Wall Marjama Bilinski & Burr

[57] ABSTRACT

These and other objectives are obtained by a hand-held apparatus for use in harvesting earthworms using a source of electrical energy having a positive terminal and a negative terminal. The apparatus has a body which has a bottom surface. The apparatus has a positive contact connected to the positive terminal and a negative contact connected to the negative terminal. A first electrically conductive wire runs from the positive contact along the bottom surface to a first terminus point and a second electrically conductive wire running from the negative contact along the bottom surface to a second terminus point, wherein the conductive wires are exposed along the bottom surface. The first electrically conductive wire and the second electrically conductive wire are in contact with the earthworm and supply an electrical current sufficient to immobilize the earthworm.

5 Claims, 3 Drawing Sheets

WORM HARVESTER

BACKGROUND OF THE INVENTION

This invention relates to the harvesting of earthworms, and more specifically to a hand-held device used in the harvesting of earthworms from the ground surface.

Earthworms have a number of beneficial uses. The most recognizable is the use of earthworms as bait for the sport fisherman. The fisherman gathers earthworms prior to setting out on the fishing expedition or purchases earthworms from a commercial vendor. In either case, the person who harvests the earthworms is faced with problems inherent in the harvesting process.

One problem in harvesting earthworms is finding earthworms that are on the ground surface and not entirely buried in the soil. This problem is solved in a number of ways, including the manual overturning of the soil in which the earthworms reside using a shovel or spade. In addition, a number of patents have issued that teach means for driving the earthworms to the surface, including U.S. Pat. No. 4,817,331 to Podsiadly et al., which teaches the utilization of electric pulses to drive earthworms to the surface for easier harvesting.

Although there are numerous references in the art which teach the use of electric current to drive earthworms to the surface, until now there remained the problem of actually physically picking up the earthworm from the ground surface. The texture, flexibility, and mobility of the earthworm makes it difficult to pick up the earthworm. The earthworm is often times able to allude the harvester by rapid movements and/or by slipping through the grip of the harvester before the harvester can apply grip pressure sufficient to immobilize the earthworm while not killing the earthworm through the use of too much pressure. It is important in the various methods of utilization of the earthworm that the earthworm remain alive until and during use, including sport fishing where a live worm presents the most desirable bait.

SUMMARY OF THE INVENTION

It is therefore a primary object of the present invention to provide an apparatus that aids in the harvest of earthworms.

It is a further object of the present invention to supply an apparatus that immobilizes an earthworm so that the earthworm may be more easily harvested.

It is yet a further object of the present invention to provide an apparatus that aids in the harvesting of live earthworms.

These and other objectives are obtained by a hand-held apparatus for use in harvesting earthworms using a source of electrical energy having a positive terminal and a negative terminal. The apparatus has a body which has a bottom surface. The apparatus has a positive contact connected to the positive terminal and a negative contact connected to the negative terminal. A first electrically conductive wire runs from the positive contact along the bottom surface to a first terminus point and a second electrically conductive wire running from the negative contact along the bottom surface to a second terminus point, wherein the conductive wires are exposed along the bottom surface. The first electrically conductive wire and the second electrically conductive wire are in contact with the earthworm and supply an electrical current sufficient to immobilize the earthworm.

BRIEF DESCRIPTION OF THE DRAWINGS

For a better understanding of these and other objects of the present invention, reference is made to the detailed description of the invention which is to be read in conjunction with the following drawings, wherein.

DETAILED DESCRIPTION OF THE INVENTION

Figure 1:
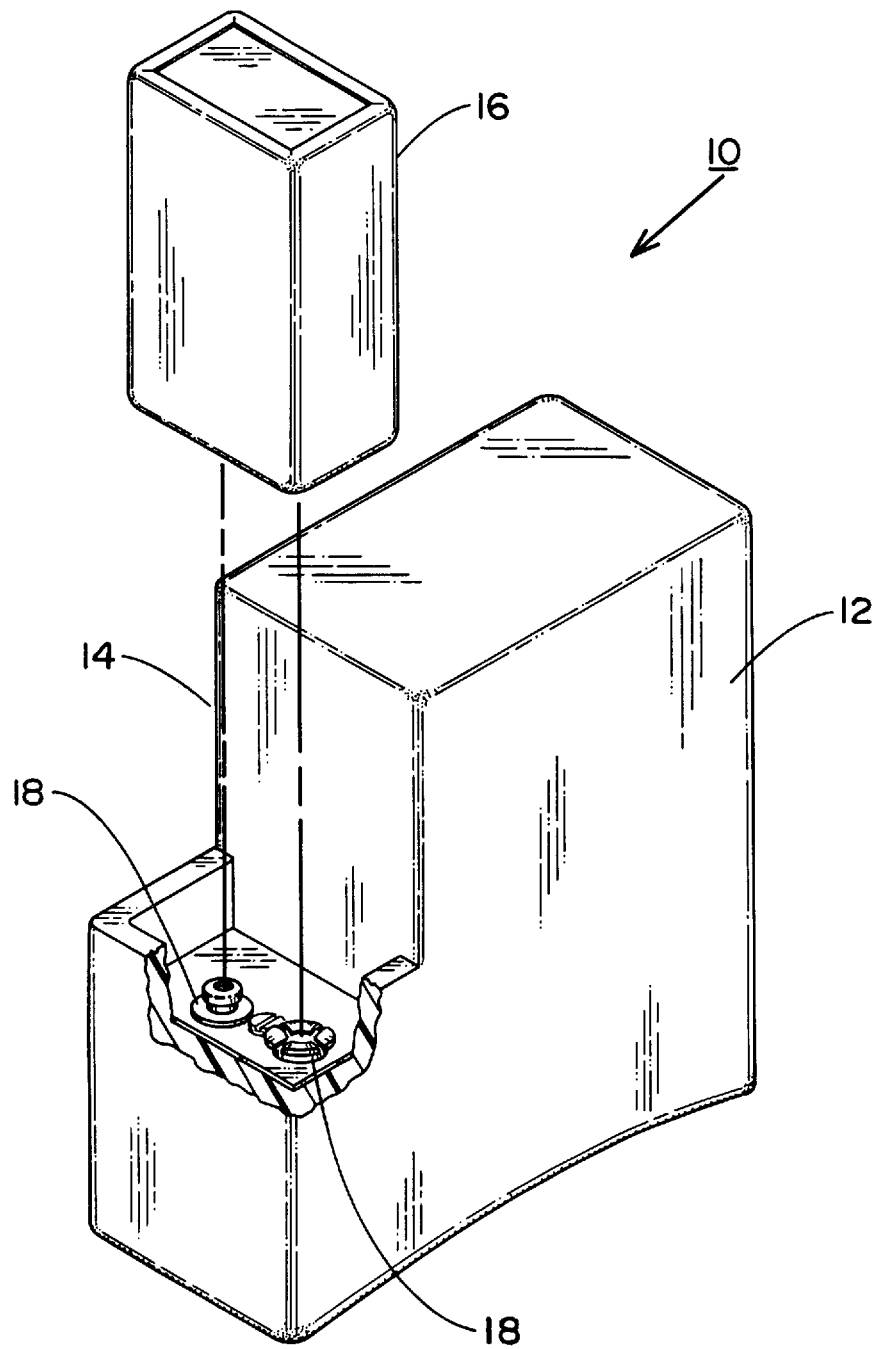
FIG. 1 is a perspective view of one embodiment of the present invention.

Referring now to FIG. 1, there is shown one embodiment of the present invention. The worm harvesting apparatus 10 includes a body 12. The body 12 is constructed of a non-electrically conductive rigid material that is shaped to fit into the user's hand. The handle may be formed of various materials and may be formed into various shapes. The user will utilize the device with one hand while picking up the earthworm with the other hand, so it is important that the device be sized and shaped in order to fit into one hand. For example, the handle may include ridges or indentations that conform to the shape of the user's fingers.

In the preferred embodiment, the body 12 has an aperture or battery containment area 14 which is formed to accept a battery 16. The preferred embodiment uses a standard 9-volt battery and the battery containment area 14 is shaped to accept that size battery. Of course, depending upon the specifications of a particular user, the size and shape of the battery and containment area may vary. The battery containment area 14 includes electrical contacts 18, one negative and one positive, permanently placed to accept the terminals 20 of the battery 16 when the battery 16 is properly placed in the battery containment area 14. As is known in the art but not shown, the electrical contacts may be connected to the body by electrically conductive wires using a pliable connector module that easily fits into the containment area and allows for engagement of the battery to the contacts at a point distant from the body at which time the battery and module are placed into the containment area, similar to the method in which a 9-volt radio battery is connected to a portable transistor radio and placed within the body of the radio.

Figures 2, 3:
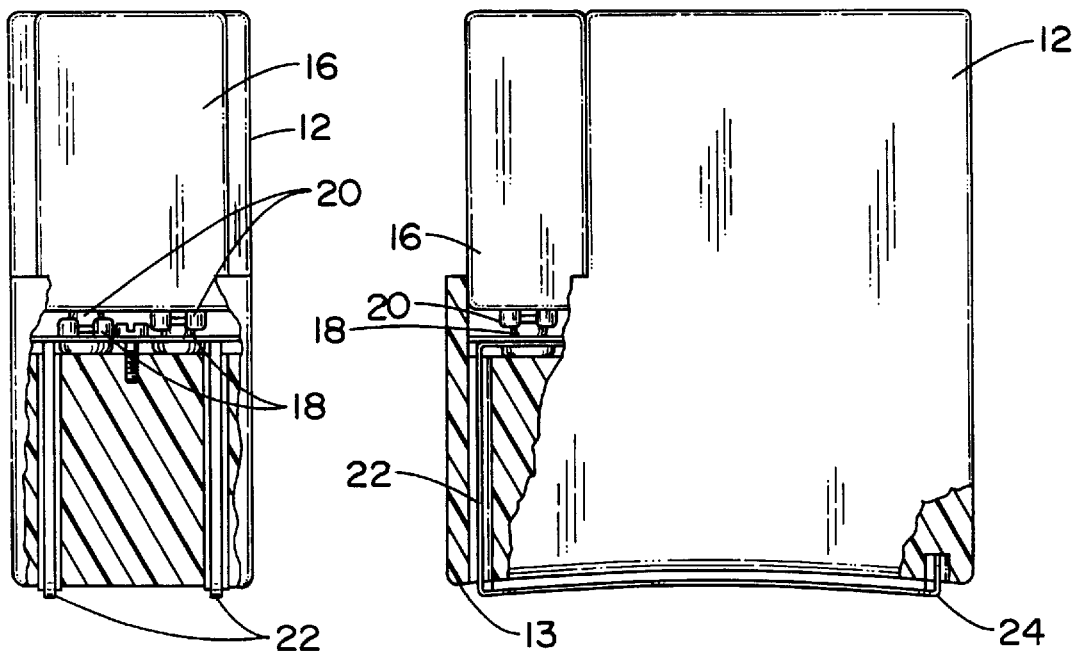
FIG. 2 is a partial cut-away side view of one embodiment of the present invention.
FIG. 3 is a partial cut-away front view of one embodiment of the present invention.
Figure 4:
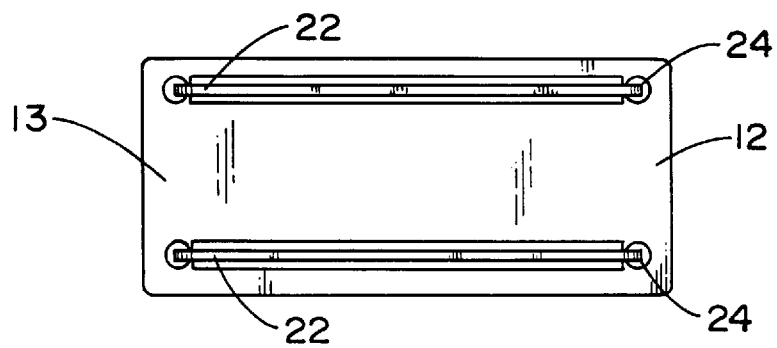
FIG. 4 is a bottom view of one embodiment of the present invention.

Referring now to FIGS. 2, 3 and 4, the battery 16 is shown in the engaged position wherein the battery 16 is supplying electrical charge to the apparatus 10. The electrical contacts 18 supply charge to electrically conductive wires 22 which run from the contacts 18 through the body 12 to the bottom side 13 of the body 12. The wires 22 run along the bottom side 13 of the body 12 and are exposed for the entire length or substantially the length of the bottom side 13 of the body 12. Each of the electrical wires 22 ends at a terminus point 24. In the preferred embodiment, the bottom side of the body is slightly arcuate along the axis of the electrical wires for reasons which become apparent below.

In use, the user sights an earthworm upon the surface of the ground. The user grasps the body of the apparatus with one hand. The user rapidly places the apparatus over and on top of the earthworm so that the electrical wires come in contact with the earthworm. Because the movement of the user is rapid, it is desirable to have just enough of an arcuate shape to the bottom so that the wires engage the earthworm but the bottom side of the body does not crush the earthworm between the body and the ground. As both wires of the apparatus contact the earthworm, an electrical current is provided to the earthworm which is sufficient to immobilize the earthworm, but not kill it, which allows the user to grasp the earthworm with the free hand.

Figure 5:
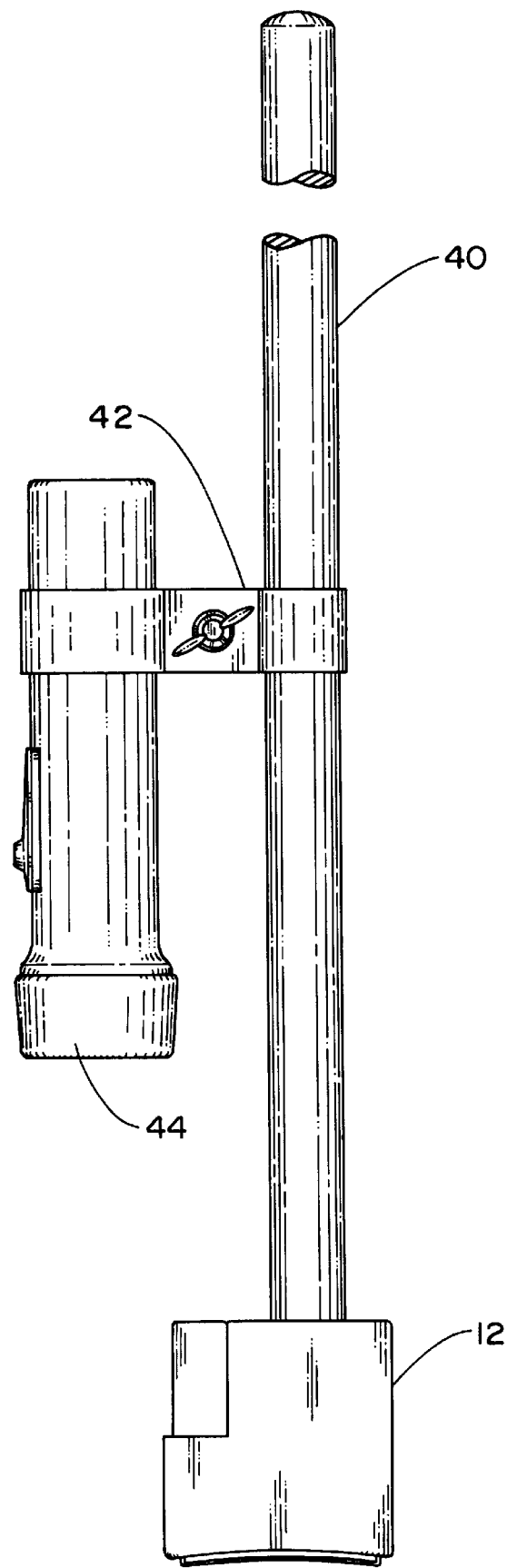
FIG. 5 is a perspective view of one embodiment of the present invention.

Referring now to FIG. 5, there is shown an embodiment of the present invention which includes a handle 40 that is attached to the body 12. The handle 40 extends vertically so that the user may operate the invention from a standing position. Preferably, the handle 40 is equipped with a clamp 42 to attach a flashlight 44 to the handle so that the apparatus may be used during periods of low light. One skilled in the art would be familiar with various means with which to attach a light source to the handle 40 so that the area immediately adjacent to the body 12 would be illuminated.

While this invention has been explained with reference to the structure disclosed herein, it is not confined to the details set forth and this application is intended to cover any modifications and changes as may come within the scope of the following claims:

What is claimed is:

1. A hand-held apparatus for use in harvesting earthworms using a source of electrical energy having a positive terminal and a negative terminal, said apparatus comprising:

a body having a bottom surface;

a positive contact connected to said positive terminal;

a negative contact connected to said negative terminal;

a first electrically conductive wire running from said positive contact along said bottom surface to a first terminus point; and, a second electrically conductive wire running from said negative contact along said bottom surface to a second terminus point, wherein said conductive wires are exposed along said bottom surface, such that said first electrically conductive wire and said second electrically conductive wire contact the earthworm and supply an electrical current sufficient to immobilize the earthworm.

2. The apparatus of claim 1 wherein said bottom surface is arcuately shaped.

3. The apparatus of claim 1 further comprising a handle attached to said body.

4. A method of immobilizing an earthworm, said method comprising the steps of;

providing a source of electrical energy having a positive terminal and a negative terminal;

providing a hand-held apparatus including a body having a bottom surface, a positive contact connected to said positive terminal, a negative contact connected to said negative terminal, a first electrically conductive wire running from said positive contact along said bottom surface to a first terminus point, and a second electrically conductive wire running from said negative contact along said bottom surface to a second terminus point, wherein said conductive wires are exposed along said bottom surface; and, placing said hand-held apparatus such that said first electrically conductive wire and said second electrically conductive wire contact the earthworm and supply an electrical current sufficient to immobilize the earthworm.

5. A method of immobilizing an earthworm, said method comprising the steps of;

providing a source of electrical energy having a positive terminal and a negative terminal;

providing a hand-held apparatus including a body having an arcuately-shaped bottom surface, a positive contact connected to said positive terminal, a negative contact connected to said negative terminal, a first electrically conductive wire running from said positive contact along said bottom surface to a first terminus point, and a second electrically conductive wire running from said negative contact along said bottom surface to a second terminus point, wherein said conductive wires are exposed along said bottom surface; and, placing said hand-held apparatus such that said first electrically conductive wire and said second electrically conductive wire contact the earthworm and supply an electrical current sufficient to immobilize the earthworm.

* * * * *